United States Patent [19]
Halpern

[11] Patent Number: 5,749,883
[45] Date of Patent: May 12, 1998

[54] MEDICAL INSTRUMENT

[76] Inventor: David Marcos Halpern, Avenida Gaona 2645, Buenos Aires, Argentina

[21] Appl. No.: 703,192

[22] Filed: Aug. 26, 1996

[30] Foreign Application Priority Data

Aug. 30, 1995 [AR] Argentina .................................. 333334

[51] Int. Cl.⁶ .................................................. A61B 17/22
[52] U.S. Cl. .......................... 606/159; 600/114; 606/106; 606/198; 604/105; 604/107
[58] Field of Search .................................. 600/114, 115, 600/116; 606/151, 108, 113, 127, 159, 191, 192, 194, 195, 198; 604/96, 105, 107

[56] References Cited

U.S. PATENT DOCUMENTS 4,921,484  5/1990  Hillstead ............................. 606/159 X
5,100,423  3/1992  Fearnot ................................. 606/159

Primary Examiner—Beverly M. Flanagan
Attorney, Agent, or Firm—Michael J. Striker

[57] ABSTRACT

A medical instrument has an elastic tubular portion formed as a weaving portion, and an actuating element arranged so that by its displacement it acts on the tubular portion so that the tubular portion assumes one position in which it is expanded radially to assume a globe shape, and another position in which it is reduced radially to assume a substantially cylindrical shape with a diameter substantially smaller than a diameter of the globe shape.

11 Claims, 2 Drawing Sheets

MEDICAL INSTRUMENT

BACKGROUND OF THE INVENTION

The present invention generally relates to medical instruments.

More particularly, it relates to a medical instrument which can be used for cytological and histological diagnosis of stenosis, for mobilization of different type of calculus, for removal of substance adhered inside the stenosed conduits, etc.

Medical instruments of the above mentioned general type are known in the art. For providing cytological and histological diagnosis of stenosis endoscopically semi-unsurmountable, the operation is performed by a small brush which, when being rubbed at the area of interest, takes samples. In order to mobilize different type of calculus, longitudinal wires coupled at the ends are utilized to trap the calculus and to draw it out of the body. This operation in connected with occasional risk of being withheld basket and calculus obliging the professionals to use another method. On the other hand, there exists at present a balloon of inflatable latex or similar function, which however is inconvenient due to its material and can be pierced easily thus becoming useless. Finally, several instruments exist for removing substances adhered inside this stenosed conduit, which however can traumatize the conduit.

SUMMARY OF THE INVENTION

Accordingly, it is an object of the present invention to provide a medical instrument of the above mentioned general type, which avoids the disadvantages of the prior art.

In keeping with these objects and with others which will become apparent hereinafter, one feature of the present invention resides, briefly stated, in a medical instrument which has a wire weaving tubular section, and an actuating element acting on the wire weaving tubular section so that it can not assume a first position in which the tubular section forms an expanded elastic globe and a second position in which the tubular section is reduced to have a diameter which is several times smaller than the diameter of the expanded globe.

When the medical instrument is designed in accordance with the present invention it eliminates the disadvantages of the prior art. When it is used for cytological and histological diagnosis of stenosis, the globe-shaped tubular portion of the instrument facilitates the operation and a greater amount of samples can be taken. It also allows a radiologist specialist to intervene at the samples taken when he considers it convenient. When the new medical instrument is utilized to mobilize different type of calculus, there is no risk either for the calculus or for the instrument to be withheld. Also, the instrument is convenient and can not be damaged easily. When the new instrument is used for removal of substance adhered inside the stenosed conduit, then due to its net weaving and its elasticity, it can be used as a complex scraper in particular for greasy substances, removing them from the conduit to which they cling, so as to provide a clean cross-section and not traumatize the conduit.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
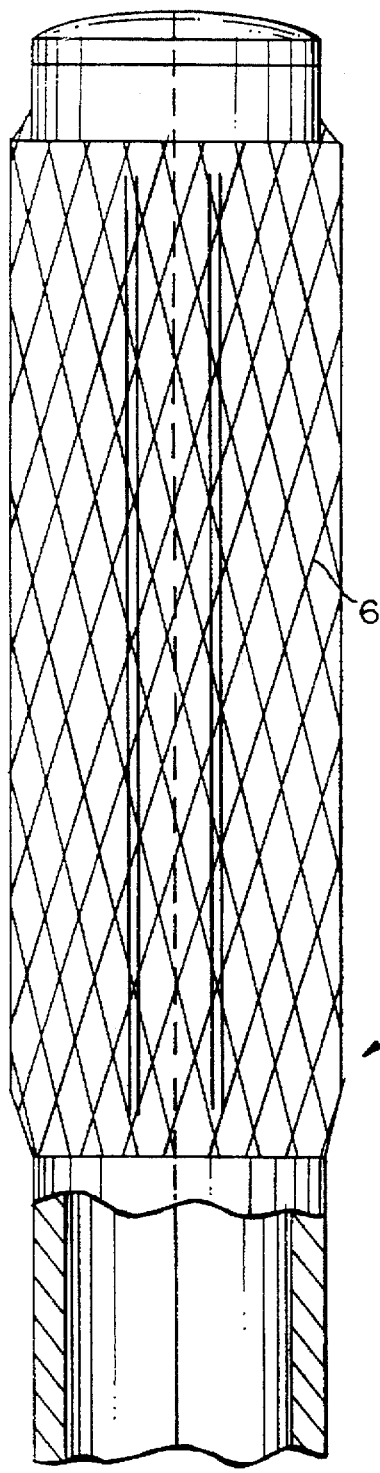
FIGS. 1 and 2 are views showing a medical instrument in accordance with one embodiment of the present invention, in two different positions.
Figure 2:
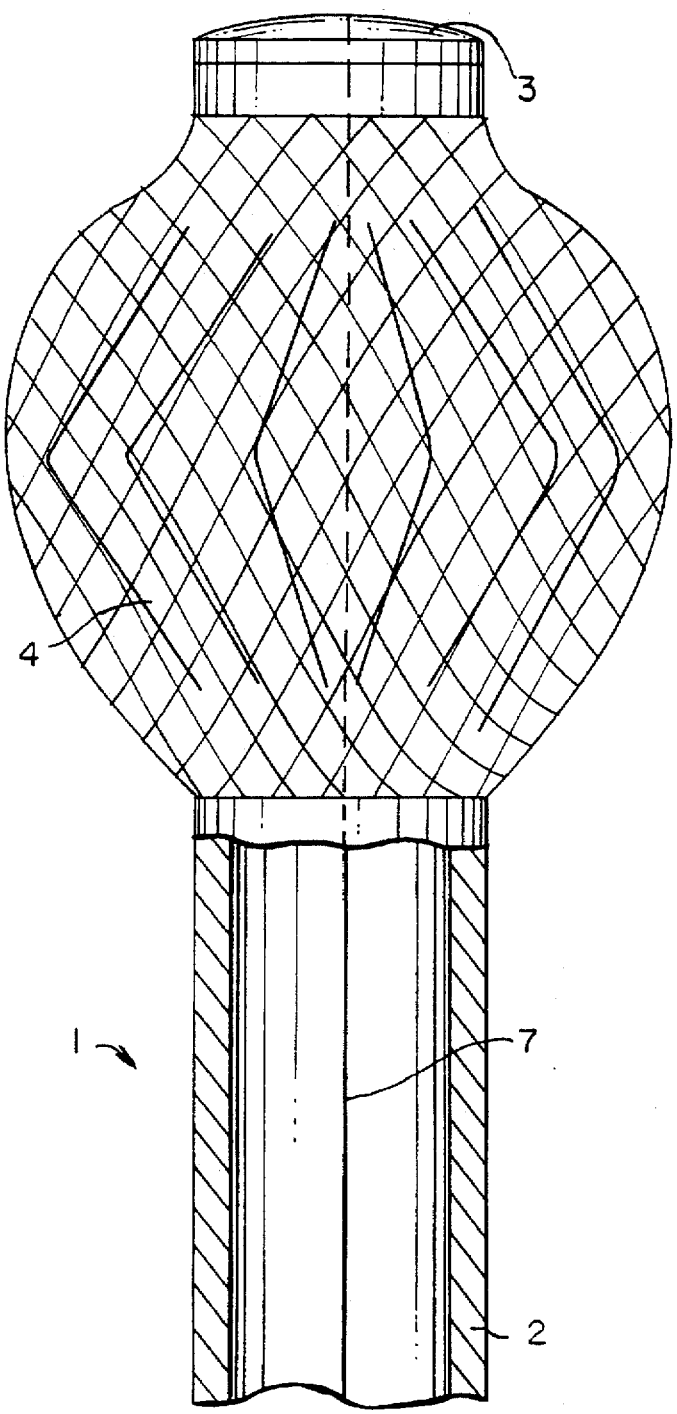

A medical instrument in accordance with a first embodiment of the present invention shown in FIGS. 1 and 2 has a tube which is identified as a whole with reference numeral 1 and can be formed as a plastic tube. The tube 1 has a proximal end portion 2 and a distal end portion 3 connected with one another by elastic longitudinal sections 4. For example, four such longitudinal sections 4 can be provided. The longitudinal sections 4 are flexible, so that the distal end 3 of the tube 1 can be displaced toward the proximal end 2 with flexing of the sections 4. For example the longitudinal sections 4 can be formed as bellows. The sections 4 can be formed as separate strips spaced from one another in a peripheral direction and separated from one another by slots.

The medical instrument in accordance with the present invention further has a tubular element identified as a whole with reference numeral 5. The tubular element 5 is formed as a weaving portion, for example a wire weaving portion composed of a plurality of wires woven in corresponding fashion. The tubular portion 5 is actually formed as a wire mesh. One axial end of the tubular portion 5 can be connected to the proximal end portion 2 of the tube 1, while the other axial end of the tubular portion 5 can be connected to the distal end portion 3 of the tube 1.

Finally, the medical instrument in accordance with the present invention has an actuating element 7 which can be formed as a wire extending through the interior of the tube 1 and the tubular portion 5. The wire 7 has a distal end connected to the distal end portion 3 of the tube 2.

In operation, the medical instrument in accordance with the present invention can assume two different positions. In a first position shown in FIG. 1, the tubular portion 5 composed of a wire mesh has a small diameter and forms a cylinder. By pulling the wire 7 downwardly in FIG. 2, the distal portion 3 is displaced toward the proximal portion 2 of the tube 1, the longitudinal sections 4 are expanded in a radial direction, and the tubular element 5 is expanded in a radial direction as well, so as to form in a second position a globe or balloon with a diameter substantially greater than the diameter of the tubular portion 5 in its position shown in FIG. 1.

Figure 3:
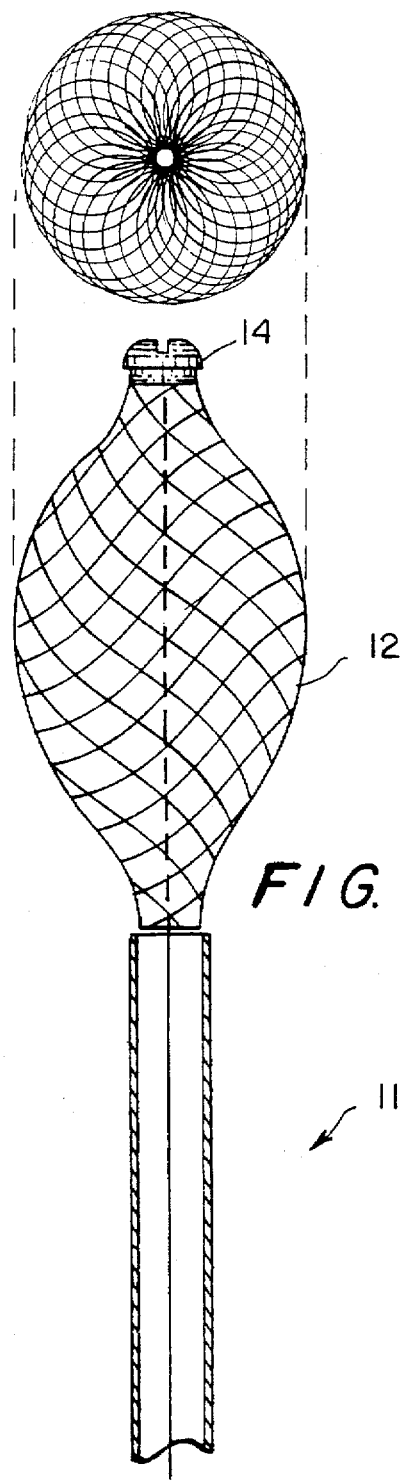
FIGS. 3 and 4 are views showing a medical instrument in accordance with another embodiment of the present invention.
Figure 4:
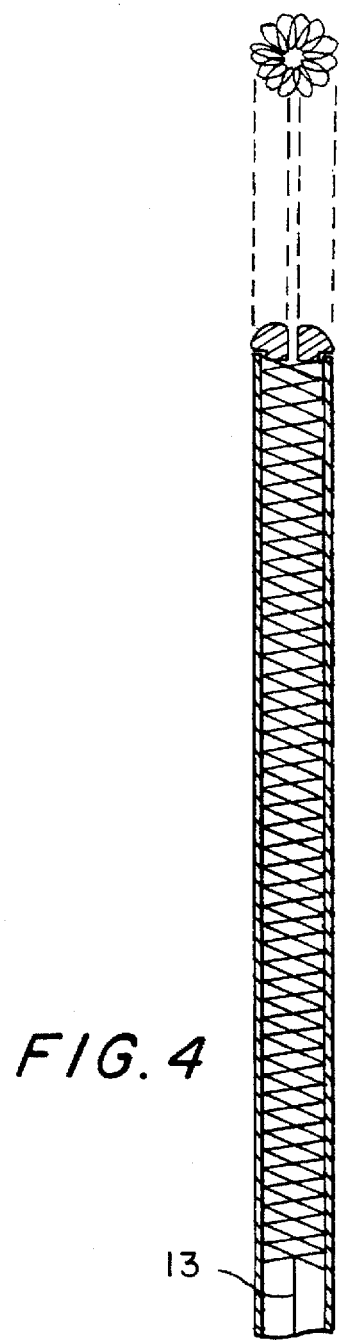
Figure 5:
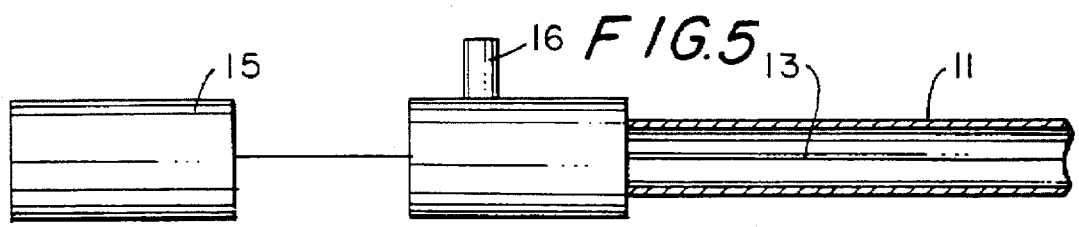
FIG. 5 is a view of the medical instrument of FIGS. 3 and 4 with additional elements.

In the embodiment shown in FIGS. 3–5, the medical instrument includes a tube identified with reference numeral 11 and a tubular portion identified with reference numeral 12. The tubular portion is formed also as a weaving portion, for example a wire weaving portion, strangled at its end to form an oval, elastic globe in the position shown in FIG. 3. The elastic tubular portion 2 formed actually as a wire mesh is actuated by an actuating element 13 formed as a wire. The free end of the tubular portion 12 is provided with a small hollow cylinder 14, through which the wire 13 can be introduced. The proximal end of the wire 13 extends outside the tube 11 and is connected with a handle 15 which allows to control the operation of the instrument. An inlet 16 is provided for supplying liquid and/or air or contrast. In the position shown in FIG. 4 the wire 13 is pulled downwardly, and the tubular portion 12 is introduced into the tube 11. In the position shown in FIG. 3, the tubular portion 12 is withdrawn from the tube 11 and due to its elasticity expands radially so as to assume the shape of a globe or balloon.

It will be understood that each of the elements described above, or two or more together, may also find a useful application in other types of constructions differing from the types described above.

While the invention has been illustrated and described as embodied in medical instrument, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters Patent is set forth in the appended claims.

I claim:

1. A medical instrument comprising: an elastic tubular portion formed as a weaving portion; and an actuating element arranged so that by its displacement it acts on said tubular portion so that said tubular portion assumes a first position in which it is expanded radially to assume a globe shape, and a second position in which it is reduced radially to assume a substantially cylindrical shape with a diameter substantially smaller than a diameter of said globe shape, said tube having a proximal end, a distal end, and elastic sections connecting said ends with one another, said actuating element having a distal end connected with said distal end of said tube so as to displace a distal end of said tube relative to said proximal end and therefore to expand said elastic sections and to straighten said elastic sections correspondingly.

2. A medical instrument as defined in claim 1, wherein said tubular portion is formed as a wire weaving portion.

3. A medical instrument as defined in claim 1, wherein said tubular portion is formed of a wire mesh.

4. A medical instrument as defined in claim 1, wherein said actuating element is formed as an elongated wire.

5. A medical instrument as defined in claim 1; and further comprising a tube associated with said tubular portion, said actuating element extending through said tube.

6. A medical instrument as defined in claim 1, wherein said elastic sections are formed as separate strips spaced from one another in a peripheral direction and separated from one another by slots.

7. A medical instrument as defined in claim 6, wherein said tubular element has opposite axial ends connected with said proximal portion and said distal portion of said tube correspondingly.

8. A medical instrument as defined in claim 1; and further comprising a tube, said actuating element extending through said tube and being connected with said tubular portion so as to pull said tubular portion into an interior of said tube so that said tubular portion assumes said second position or to withdraw said tubular portion outwardly beyond said tube so that said tubular portion assumes said first position.

9. A medical instrument as defined in claim 8, wherein said tubular portion has a distal end provided with a hollow cylinder, said actuating member extending through said hollow cylinder at said distal end.

10. A medical instrument as defined in claim 9; and further comprising a handle, said actuating element having a proximal end connected with said handle outside of said tubular portion.

11. A medical instrument as defined in claim 1; and further comprising an inlet for supplying a medium selected from the group consisting of liquid, air and contrast.

* * * * *